United States Patent
Kinnane et al.

(10) Patent No.: US 8,524,253 B2
(45) Date of Patent: Sep. 3, 2013

(54) BONE REGENERATION DEVICE

(75) Inventors: Keith Matthew Kinnane, Bartlett, TN (US); Susan J. Drapeau, Cordova, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 961 days.

(21) Appl. No.: 12/323,093

(22) Filed: Nov. 25, 2008

(65) Prior Publication Data

US 2010/0129415 A1    May 27, 2010

(51) Int. Cl.
*A61K 9/00*    (2006.01)

(52) U.S. Cl.
USPC .......... 424/400; 424/422; 424/116; 424/93.1; 514/7.6; 514/7.4

(58) Field of Classification Search
None
See application file for complete search history.

(56) References Cited

U.S. PATENT DOCUMENTS

| | | | |
|---|---|---|---|
| 6,886,568 B2 | 5/2005 | Frondoza et al. | |
| 6,893,462 B2 | 5/2005 | Buskirk et al. | |
| 7,252,685 B2 | 8/2007 | Bindseil et al. | |
| 7,351,262 B2 | 4/2008 | Bindseil et al. | |
| 7,435,260 B2 | 10/2008 | Ferree | |
| 7,498,040 B2 * | 3/2009 | Masinaei et al. | 424/400 |
| 2007/0082057 A1 | 4/2007 | Masinaei et al. | |
| 2007/0082058 A1 | 4/2007 | Masinaei et al. | |
| 2007/0248575 A1 | 10/2007 | Connor et al. | |
| 2008/0069893 A1 | 3/2008 | Masinaei et al. | |
| 2008/0077252 A1 | 3/2008 | Mills et al. | |

FOREIGN PATENT DOCUMENTS

WO    WO 2008/073628 A2 *    6/2008

* cited by examiner

*Primary Examiner* — Elizabeth C Kemmerer
(74) *Attorney, Agent, or Firm* — Sorell Lenna & Schmidt LLP (57) ABSTRACT

This invention is directed to a bone regeneration device including fascia and demineralized bone matrix mixed at a temperature not exceeding about 40° C. and lyophilized into the bone regeneration device, methods of preparing such a bone regeneration device and methods of treating bone defects using such a bone regeneration device.

6 Claims, 1 Drawing Sheet

BONE REGENERATION DEVICE

BACKGROUND

Bone grafting is a surgical procedure by which new bone or a replacement material is placed into spaces between or around fractures or holes in bone (bone defects) to aid in healing. Bone grafting is used to repair bone fractures that are extremely complex, pose a significant risk to the patient or fail to heal properly. Bone graft is also used to help fusion between vertebrae, correct deformities or provide structural support for fractures of the spine. In addition to fracture repair, bone graft is used to repair defects in bone caused by birth defects, traumatic injury, or surgery for bone cancer.

A wide variety of bone graft materials have been used and/or suggested in the art for the treatment of bone defects. Traditional bone grafting has included the use of autograft bone or allograft bone. In addition to traditional bone grafting, a number of synthetic bone graft substitutes have been used or explored, including some materials that contain ceramics, calcium phosphates or demineralized bone matrix (sometimes referred to as "DBM"). DBM is demineralized allograft bone with osteoinductive activity. Demineralized bone matrices are prepared by acid extraction of allograft bone, resulting in the loss of most of the mineralized component but retention of collagen and noncollagenous proteins including growth factors. The efficacy of a demineralized bone matrix as a bone-graft substitute or extender is due to the presence of bone morphogenetic protein (BMP) as well as the ratios of the different BMPs present. BMPs belong to the transforming growth factor (TGF) superfamily of proteins. DBM has been shown to exhibit the ability to induce and/or conduct the formation of bone. It is thus desirable to implant and maintain demineralized bone matrix at a site at which bone growth is desired.

However, the beneficial nature of demineralized bone matrix is susceptible to disruption by the incorporation of incompatible materials or techniques when formulating a medical implant. At the same time, it is desirable to have implant devices exhibiting good physical integrity to retain the demineralized bone matrix at the implant site, and that handle well in the operating environment and during implantation. In addition, it is of considerable commercial significance that the medical implant be manufacturable without undue cost, equipment or material burdens. Accordingly, there exist needs for product configurations including DBM which exhibit the ability to induce and/or support bone growth through the desired region, which are readily manufacturable and which demonstrate acceptable handling properties for surgeons.

SUMMARY

New devices and methods are provided that effectively induce and/or support bone growth through a desired region. In various embodiments, easily manufacturable devices are provided that demonstrate exceptional handling properties for surgeons. Methods of manufacturing or preparing bone regeneration devices are also provided that result in devices implanted in patients with minimal physical and psychological trauma to patients.

In one exemplary embodiment, a bone regeneration device is provided. The bone regeneration device comprises fascia and demineralized bone matrix mixed at a temperature not exceeding about 40° C. (or with the essential absence of heating at a temperature above 40° C.) and lyophilized into the bone regeneration device. The fascia and demineralized bone matrix may be mixed at a temperature not exceeding about 25° C. The amount of fascia in the device is between about 1% to 45% of the dry weight of the bone regeneration device and the amount of demineralized bone matrix in the device is between about 55% to 99% of the dry weight of the bone regeneration device. The dry weight ratio of fascia to demineralized bone matrix may be between about 1:15 to 1:1. The bulk density of the bone regeneration device may be between about 0.1 g/cc to 0.4 g/cc. The bone regeneration device may also comprise one or more pharmaceutical agents selected from the group consisting of growth factors, statins, cells, antibiotics, and immunosuppressants.

In another exemplary embodiment, a method of treating a bone defect in a subject comprising placing in the bone defect a bone regeneration device comprising fascia and demineralized bone matrix is provided. The bone regeneration device is prepared by (a) mixing a slurry of fascia with demineralized bone matrix with the essential absence of heating at a temperature above 40° C. to form a fascia-demineralized bone matrix slurry; (b) removing excess liquid from the fascia-demineralized bone matrix slurry; and (c) lyophilizing the resulting slurry from step (b) into the bone regeneration device.

The method may also include adding one or more pharmaceutical agents to the fascia-demineralized bone matrix slurry prior to step (b). The pharmaceutical agent or agents may be selected from the group consisting of growth factors, statins, cells, antibiotics, and immunosuppressants.

Alternatively, the method may comprise wetting the bone regeneration device with one or more pharmaceutical agents prior to placing the bone regeneration device in the bone defect. The pharmaceutical agent or agents may be selected from the group consisting of growth factors, statins, cells, antibiotics, and immunosuppressants. In various embodiments, the bone regeneration device is wetted with a pharmaceutical agent comprising a growth factor selected from the group consisting of BMP-2, rhBMP-2, BMP-4, rhBMP4, BMP-6, rhBMP-6, BMP-7, rhBMP-7, GDF-5, rhGDF-5, functional fragments thereof and combinations thereof. In various embodiments, the bone regeneration device is wetted with a pharmaceutical agent comprising BMP-2 or rhBMP-2.

In yet another exemplary embodiment, a method of preparing a bone regeneration device is provided. The method comprises (a) mixing a soft tissue with a liquid with the essential absence of heating at a temperature above 40° C. to form a soft tissue slurry; (b) adding a bone derived material to the soft tissue slurry; (c) mixing the bone derived material and the soft tissue slurry with the essential absence of heating at a temperature above 40° C. to form a soft tissue-bone derived material slurry; (d) removing excess liquid from the soft tissue-bone derived material slurry; and (e) lyophilizing or freeze-drying the soft tissue-bone derived material slurry resulting from step (d) into the bone regeneration device. The soft tissue may comprise fascia and the bone derived material may comprise one or more of demineralized bone matrix, partially demineralized bone matrix and non-demineralized bone matrix.

The method may also comprise adding one or more pharmaceutical agents to the soft tissue-bone derived material slurry prior to step (d). The pharmaceutical agent or agents may be selected from the group consisting of growth factors, statins, cells, antibiotics, and immunosuppressants.

Alternatively, the method may comprise wetting the bone regeneration device with one or more pharmaceutical agents after step (e). The pharmaceutical agent or agents may be selected from the group consisting of growth factors, statins, cells, antibiotics, and immunosuppressants. In various embodiments, the bone regeneration device is wetted with a pharmaceutical agent comprising a growth factor selected from the group consisting of BMP-2, rhBMP-2, BMP-4, rhBMP4, BMP-6, rhBMP-6, BMP-7, rhBMP-7, GDF-5, rhGDF-5, functional fragments thereof and combinations thereof.

In still yet another exemplary embodiment, a slurry for preparing a bone regeneration device is provided. The slurry may comprise about 1 to 50% by weight fascia and about 1 to 50% by weight demineralized bone matrix mixed with the essential absence of heating at a temperature above 40° C. The slurry may comprise one or more pharmaceutical agents selected from group consisting of growth factors, statins, cells, antibiotics, and immunosuppressants.

The pharmaceutical agent in various device and method embodiments may comprise a growth factor which may be selected from the group consisting of BMP-2, rhBMP-2, BMP-4, rhBMP4, BMP-6, rhBMP-6, BMP-7, rhBMP-7, GDF-5, rhGDF-5, functional fragments thereof and combinations thereof.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the FIGURE is not drawn to scale. Further, the relation between objects in the FIGURE may not be to scale, and may in fact have a reverse relationship as to size. The FIGURE is intended to bring understanding and clarity to the structure of the object shown, and thus, some features may be exaggerated in order to illustrate a specific feature of the structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a bone regeneration device" or "device" includes one, two, three or more devices.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New devices and methods are provided that effectively induce and/or support bone growth through a desired region. Methods of manufacturing or preparing bone regeneration devices are also provided that result in devices implanted in patients with minimal physical and psychological trauma to patients.

In various embodiments, a bone regeneration device is provided which includes bone derived material and soft tissue that is mixed together at an ambient temperature or a temperature not exceeding 40° C. (or with the essential absence of heating at a temperature above 40° C.). The bone regeneration device can be molded to a desired shape during production and then retain that shape after the device is rehydrated prior to implantation. Also, the bone regeneration device is osteoinductive and osteoconductive. In addition, the bone regeneration device does not cause an adverse immune response in a subject even though it may contain proteins, polysaccharides, lipids, and other components that are known to stimulate an immune response when implanted in a subject.

The bone derived material may be DBM, partially demineralized bone matrix, non-demineralized bone or a combination thereof. More specifically, the DBM may be DBM chips, DBM fibers, DBM wafers and/or DBM powder. The bone derived material may include more than one type of bone tissue (e.g., cancellous, cortical, or corticocancellous bone).

As stated above, demineralized bone matrix is prepared by acid extraction of bone, resulting in loss of most of the mineralized component but retention of collagen and noncollagenous proteins, including growth factors. DBM as used in the present application has approximately less than 8% by weight of residual calcium. Demineralization involves treating the surface of a bone tissue to remove a surface layer of its inorganic mineral hydroxyapatite material leaving the mechanical properties of the organic phase of the bone constructs substantially unchanged. The level of demineralization of a bone tissue is defined by the amount (weight %) of residual calcium found in the demineralized bone.

Generally, bone from an allogenic source is used to prepare DBM, but bone from a xenogenic source can also be used to prepare DBM. Methods for preparing DBM are well-known and can be found in U.S. Pat. Nos. 5,073,373; 5,484,601; and 5,284,655, which are herein incorporated by reference thereto. DBM is commercially available and can be purchased from Regeneration Technologies, Inc. (Alachua, Fla.) and The American Red Cross (Arlington, Va.), among others.

Partially demineralized bone matrix is bone that has underwent an acid extraction similar to DBM but for a shorter period of time. This results in more than about 8% by weight of calcium and other minerals in the finished product. The partially demineralized bone matrix has up to about 30% by weight of calcium and other minerals.

Non-demineralized bone is bone that has not undergone an acid extraction and contains an amount of calcium and other minerals which typically found in normal bone.

In various embodiments, the bone derived material may have a particle size ranging from about 25µ to about 2000µ, from about 50µ to about 1500µ, from about 100µ to about 1500µ, from about 100µ to about 1000µ, or from about 125µ to about 750µ. Bone derived material having such particle sizes can be obtained by grinding bone and then passing the resulting ground bone particles through a sieve having a particular pore size that is not larger than the upper end of the range. With DBM and partial demineralized bone matrix, the bone derived material is then subjected to acid extraction. Alternatively, with DBM and partial demineralized bone matrix, large pieces or chunks of bone can first be demineralized and then grinded and passed through a sieve with the appropriate pore size.

In various embodiments, ribbons, segments, fibers, wafers and other shapes of bone derived material are used and have a length ranging from 0.1 to 15 mm and a width ranging from 0.1 to 10 mm and a thickness ranging from 0.1 to 4 mm. The ratio of the width to length for ribbons, fibers, wafers can range from 1:1 to 1:100.

It is well known to one of ordinary skill in the art that DBM, partially demineralized bone matrix and non-demineralized bone may become a gelatin when heated above 55° C. During preparation or manufacturing of a bone regeneration device of the present invention, the temperature at which the components of the bone regeneration device are mixed does not exceed about 40° C. The bone derived material does not become a gelatin. In addition, any proteins contained within the DBM, partially demineralized bone matrix or non-demineralized bone are not denatured or inactivated during the manufacturing of the device. It is believed that these proteins retain full activity.

The soft tissue may be muscle or tissue rich in collagen or a combination of both. Examples of the type of muscle that may be used include smooth muscle, cardiac muscle and skeletal muscle. Non-limiting examples of tissue rich in collagen that may be used include, fascia, connective tissue (including crudely fragmented connective tissue), skin (hide), tendons, ligaments, articular cartilage, intestine, pericardium, intervertebral discs, dura mater and the tunica submucosa layer of the small intestine. Different types of fascia may be used in various embodiments including: fascia lata, fascia adherens, fascia brachii, fascia axillaris, antebrachial fascia, abdominal fascia, internal fascia, fascia iliaca, fascia profunda, clavipectoral fascia, fascia cribosa, crucial fascia, deltoid fascia, dorsal deep fascia, pelvic fascia, fascia cruris, lumbar fascia, and pectoral fascia, among others. The term "fascia" is used herein and can include any of these types of fascia. "Crudely fragmented connective tissue" refers to connective tissue that has been sliced, ground, carved, chipped, chopped, minced, cut, dissected, rent, ripped, sectioned, snipped, diced, shaved, comminuted, or trimmed into fragments having an average diameter greater than about 50 microns and less than about 0.5 cm (i.e., having cut dimensions of approximately 0.5×0.5 cm), and thickness appropriate to the tissue being crudely fragmented. In some embodiments, the crude fragments may not be of uniform size.

In various embodiments, the soft tissue includes fascia obtained from the thigh of an animal. It has a high collagen content but it also can contain elastin and other non-collagenous proteins. Fascia can be obtained from any tissue bank such as Community Tissue Services ("CTS") located in Dayton, Ohio.

The soft tissue may be cut into square, rectangular or other shaped pieces having an approximate length ranging from about 0.1 mm to about 100 mm, from about 1 mm to about 50 mm, or from about 3 mm to about 20 mm per side. Soft tissues such as fascia can typically range from about 0.1 to about 3 mm in thickness. The collagen-rich tissue is washed with cold water to remove particles of debris.

Tissue rich in collagen is distinct from purified collagen. While collagen makes up a large percentage of the protein component of the various tissue rich in collagen, the tissue rich in collagen may also contain non-collagenous proteins, lipids, polysaccharides, polynucleotides, cells, and other cellular and extra-cellular components. It is well-known in the field that purified collagen is a relatively weak immunogen which makes purified collagen very useful for implantation into a subject. It is also well-known that tissue, in general, and specifically tissue rich in collagen can be highly immunogenic and is not very useful for implantation into a subject. (See for example U.S. Pat. No. 6,127,143 at column 2, line 56 through column 3, line 34, the contents of which are incorporated by reference thereto). A method of reducing the immunogenicity of tissue includes inactivating the various immunogenic components, such as by heating to greater than 115.6° C. As the bone regeneration device of the present invention is manufactured or prepared with the essential absence of heating at a temperature above 40° C., the potential antigens present in muscle and tissue rich in collagen are present. As such, it was unexpected that the bone regeneration device prepared by mixing bone derived material and soft tissue at a temperature not exceeding 40° C. (or with the essential absence of heating at a temperature above 40° C.) would result in a device that does not cause an adverse immunogenic response in an animal when the device is inserted or implanted in the animal. Rather, this novel bone regeneration device provides a good scaffold for the growth of bone even though the soft tissue may contain highly immunogenic components.

In various embodiments, the bone derived material and the soft tissue may be derived from allogenic or xenogenic sources. In some embodiments, the bone derived material and the soft tissue are obtained from vertebrate species, for example, human, bovine, porcine, ovine, caprine, and fish. The bone derived material may include bone from a single donor source or from multiple donor sources and the soft tissue may also include soft tissue from a single donor source or from multiple donor sources. In certain embodiments, the bone derived material and the soft tissue are derived from the same animal including a human.

The bone derived material may range on a dry weight basis from approximately 25% to approximately 99.99% of the bone regeneration device. In various embodiments, the bone derived material may be approximately 30% to approximately 80%, or approximately 40% to approximately 70% of the dry weight basis of the bone regeneration device. The soft tissue may range on a dry weight basis from approximately 0.01% to approximately 50% of the bone regeneration device.

In various embodiments, the soft tissue may be approximately 5% to approximately 40%, or approximately 10% to approximately 30% of the bone regeneration device.

The ratio based on dry weight of soft tissue to bone derived material may be from about 1:15 to about 1:1, or about 1:10 to 1:1, or about 1:5 to about 1:1 and ranges therebetween. The ratio based on wet weight of soft tissue to bone derived material may be from about 1:0.01 to about 1:50, or about 1:0.1 to 1:5 and ranges therebetween.

Figure 1:
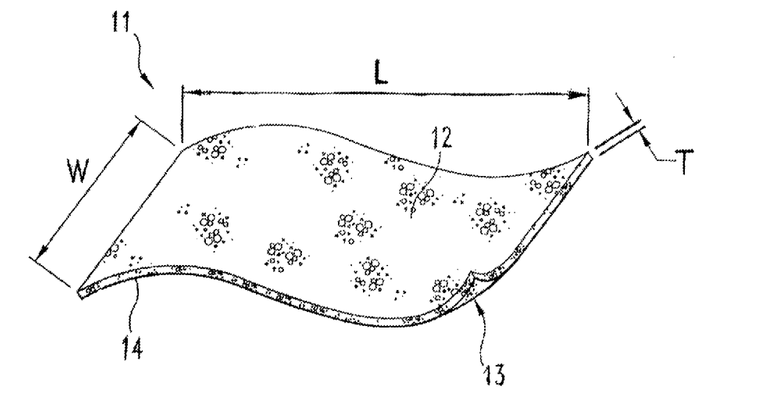
FIG. 1 provides a perspective view of a DBM-containing medical device of the invention.

The bone regeneration device may be manufactured in a ready-to-use condition and packaged in medically acceptable packaging in sterile condition in either wet or dry formats. In one exemplary embodiment, as illustrated in FIG. 1, the ready-to-use medical product can be a porous solid sheet 11. The bone regeneration device can be configured as strips or other parallelepiped three-dimensional bodies which are readily manufacturable. The bone regeneration device as a sheet includes a first face 12, a second face 13 and sidewalls 14 interconnecting the first and second faces 12 and 13, respectively. In this embodiment, the bone regeneration device can have any suitable length L, width W and thickness T. In various embodiments, the length and width will range from about 1 mm to about 200 mm, and the thickness will range from about 0.1 mm to about 10 mm. More typically, the length and width will each range from about 1 mm to about 100 mm, and the thickness from about 0.2 mm to about 1 mm. Even more typically, the length and width may be in the range of from about 1 mm to about 50 mm and the thickness may be from about 0.2 mm to about 1 mm. From the standpoint of volume, in various embodiments, bone regeneration devices may have a unitary body defining a volume of about 0.1 mm$^3$ to about 40 cm$^3$, in the range of about 500 mm$^3$ to about 10,000 mm$^3$, and/or in the range of about 600 mm$^3$ to about 10,000 mm$^3$. Exemplary dimensions include, but are not limited to, approximately 100 mm×20 mm×5 mm; approximately 50 mm×20 mm×5 mm; approximately 10 mm×12 mm×5 mm and/or approximately 8 mm×25 mm×5 mm. Linear and volumetric dimensions within the ranges provided above may be employed within the scope of the present invention.

The bulk density of a bone regeneration device of the present invention may vary and depend upon factors such as the porosity, the density of the incorporated materials and the hydration level of the bone regeneration device. In certain embodiments, the bone regeneration device is dehydrated (i.e., containing less than 5% by weight of water or other liquid), and has a bulk density in the range of from about 0.1 g/cc to about 0.4 g/cc, from about 0.1 g/cc to about 0.3 g/cc or from about 0.15 g/cc to about 0.25 g/cc. Nonetheless, as noted above, these densities may vary with many factors. Thus, a bulk density within these ranges, or one that is lower or higher may be exhibited by the devices of the present invention.

A bone regeneration device according to the present invention may be substantially porous. A bone regeneration device may have a void volume of at least about 40% and typically in the range of about 40% to about 90% especially when the bone regeneration device is dehydrated. Void volumes of about 50% to less than about 70% or in the range of about 70% to about 90% or more, is achieved by varying the amount of water or other liquid present, or by changing the amount of soft tissue, bone derived material or other components used to prepare the bone regeneration device and/or varying the lyophilization conditions.

A bone regeneration device according to the present invention is manufactured by mixing soft tissue with bone derived material at a temperature not exceeding about 40° C. or with the essential absence of heating at a temperature above 40° C.

In one exemplary embodiment, demineralized bone matrix and fascia are mixed. In another embodiment, DBM and partially demineralized bone matrix is mixed with fascia and/or other tissue rich in collagen. In some embodiments, the soft tissue is mixed with water prior to adding in the bone derived material, but in other embodiments the bone derived material is mixed with water first and the soft tissue is then added. In some embodiments, fascia and DBM are mixed together in a Waring blender which mixes at a high speed. Alternatively, one can utilize slower speeds of mixing during the manufacturing of the bone regeneration device. Without wishing to be bound to theory, it is believed that the mixing of the bone derived material and soft tissue with a liquid at a high speed allows for the incorporation of air into the mixture and allows for the liquid to be trapped between the solid particles. As the bone regeneration device dries, the water evaporates to create voids throughout the bone regeneration device. Thus, methods of mixing the soft tissue and bone derived material to create voids upon drying of the bone regeneration device are useful.

In various embodiments, soft tissue is mixed with water and then bone derived material is added the slurry is mixed. Liquids other than water may be used. Examples of liquids that may be used during the manufacturing or preparation of a bone regeneration device include sterile water, physiological saline, phosphate buffered saline and the like. In some embodiments, a majority of the liquid may be removed from the bone regeneration device during manufacturing or preparation thereby allowing the device to be sold in a dry form. In some embodiments, the bone regeneration device may be sold in a wet form in which a portion of the liquid present during the manufacture or preparation is still present when the device is sold (usually about 5% or more of the liquid present during manufacturing or preparation). The drying of the bone regeneration device during its manufacture or preparation (also referred to as the removal of the water or other liquid used during its manufacture or preparation) may be conducted utilizing lyophilization or other sublimation drying techniques that involve freezing the wet material and drying the material while frozen. The mixture of soft tissue and bone derived material may be placed in a liquid-penetrable mold, such as a porous mold, to obtain a desired shape. The material is then dried resulting in a bone regeneration device having the shape of the mold.

During the manufacture or preparation of the bone regeneration device, one or more pharmaceutical agents may be added. Alternatively, one or more pharmaceutical agents may be adsorbed into or on the bone regeneration device prior to implantation of the bone regeneration device in a subject. This may be done by wetting the bone regeneration device with one or more pharmaceutical agents. Alternatively, one or more pharmaceutical agents may be coated on the bone regeneration device prior to implantation in a subject. The pharmaceutical agents can include, but are not limited to, growth factors, statins, cells, antiprotozoal agents, antibiotics, antimyobacterial agents, antifungal agents, antiviral agents, antineoplastic agents, immunosuppressants, immunostimulants, blood calcium regulators, agents useful in glucose regulation, anticoagulants, antithrombotics, antihyperlipidemic agents, cardiac drugs, thyromimetic and antithyroid drugs, adrenergics, antihypertensive agents, cholnergics, anticholinergics, antispasmodics, antiulcer agents, skeletal and smooth muscle relaxants, prostaglandins, local anesthetics, analgesics, narcotic antagonists, antitussives, sedative-hypnotic agents, anticonvulsants, antipsychotics, anti-anxiety agents, antidepressant agents, anorexigenics, antioxidants, vaso-active agents, bone-active agents, osteogenic factors, antiarthritic agents, and diagnostic agents. The amount of the one or more pharmaceutical agent within the bone regeneration device, when present, can range from about 0.001% dry weight to about 25% dry weight, or about 0.01% dry weight to about 15% dry weight. Various other substances can be added such as, but not limited to, preservatives, suspending agents, buffering agents, viscosity changing agents, pH adjusters and excipients to the bone regeneration device during manufacture or preparation of a device or prior to implantation of a device in a subject. The amount of the various other substances if added to a bone regeneration device may be in the range of from about 0.0001% dry weight to about 10% dry weight, or about 0.001% dry weight to about 1% dry weight.

In various embodiments, the one or more pharmaceutical agents include a growth factor. The growth factor may be an osteoinductive protein or molecule that may be used alone or in combination with any other pharmaceutical agent. Platelet-derived growth factors (PDGFs), bone morphogenetic proteins (BMPs), insulin-like growth factors (IGFs), basic fibroblast growth factor (bFGF), cartilage derived morphogenetic protein (CDMP), growth and differentiation factors (GDFs), LIM mineralization proteins, transforming growth factor beta family (TGF-β), and other bone proteins, such as CD-RAP, are all growth factors that can be used in a bone regeneration device of the present invention. These proteins can be recombinantly produced or obtained and purified from an animal that makes the proteins without the use of recombinant DNA technology. Recombinant human BMP is referred to as "rhBMP"; recombinant human GDF is referred to as "rhGDF". Mimetics of these growth factors can also be used in the devices of the present invention for inducing the growth of bone. A detailed discussion of how some of these growth factors and/or proteins induce bone growth may be found in Rengachary, *Neurosurg. Focus*, 13:1-6, 2002; Reddi, *Arthritis Res*, 3:1-5, 2001; and Varkey et al., *Expert Opin. Drug Deliv.*, 1:19-36, 2004.

Examples of BMPs and GDFs known to have osteogenic, chondrogenic and other growth and differentiation activities and are suitable for this invention include, but are not limited to, BMP-2, rhBMP-2, BMP-3, rhBMP-3, BMP-4 (also referred to as BMP-2B), rhBMP4 (also referred to as rhBMP-2B), BMP-5, rhBMP-5, BMP-6, rhBMP-6, BMP-7 (OP-1), rhBMP-7 (rhOP-1), BMP-8, rhBMP-8, BMP-9, rhBMP-9, BMP-12, rhBMP-12, BMP-13, rhBMP-13, BMP-15, rhBMP-15, BMP-16, rhBMP-16, BMP-17, rhBMP-17, BMP-18, rhBMP-18, GDF-1, rhGDF-1, GDF-3, rhGDF-3, GDF-5, rhGDF-5, GDF-6, rhGDF-6, GDF-7, rhGDF-7, GDF-8, rhGDF-8, GDF-9, rhGDF-9, GDF-10, rhGDF-10, GDF-11, rhGDF-11, GDF-12, rhGDF-12, GDF-14 and rhGDF-14. BMP-2, BMP-3, BMP-4, BMP-5, BMP-6 and BMP-7 are disclosed in U.S. Pat. Nos. 5,108,922; 5,013,649; 5,116,738; 5,106,748; 5,187,076; and 5,141,905; BMP-8 is disclosed in PCT publication WO91/18098; BMP-9 is disclosed in PCT publication WO93/00432; BMP-10 is disclosed in U.S. Pat. No. 5,637,480; BMP-11 is disclosed in U.S. Pat. No. 5,639,638; BMP-12 and BMP-13 are disclosed in U.S. Pat. No. 5,658,882; BMP-15 is disclosed U.S. Pat. No. 5,635,372; and BMP-16 is disclosed in U.S. Pat. Nos. 5,965,403 and 6,331,612. Growth and differentiation factors (GDFs) are described in PCT applications WO94/15965; WO94/15949; WO95/01801; WO95/01802; WO94/21681; WO94/15966; WO95/10539; WO96/01845; WO96/02559 and others. All of the afore-mentioned references are incorporated herein by reference thereto.

Other growth factors that may be added to the bone regeneration devices of the present invention include BIP which is disclosed in WO94/01557, HP00269 which is disclosed in JP Publication number: 7-250688 and MP52 which is disclosed in PCT application WO93/16099. Other agents that can be included in the devices of the present invention include heterodimers of the above-mentioned growth factors, modified proteins, partial deletion products and mimetic agents. These proteins may be used individually or in mixtures of two or more.

Each BMP may be homodimeric, or may be heterodimeric with other BMPs (e.g., a heterodimer composed of one monomer each of BMP-2 and BMP-6) or with other members of the TGF-β superfamily, such as activins, inhibins and TGF-β 1 (e.g., a heterodimer composed of one monomer each of a BMP and a related member of the TGF-β superfamily). Examples of such heterodimeric proteins are described for example in PCT application WO 93/09229. The amount of osteogenic protein useful herein is an amount which is effective to stimulate increased osteogenic activity of infiltrating progenitor cells and will depend upon several factors including the size and nature of the defect being treated, the bone regeneration device, and the particular protein being employed.

One or more statins may also be included in devices of the present invention. Statins are 3-hydroxy-3-methylglutaryl coenzyme A reductase (a.k.a. HMG-CoA reductase) inhibitors and have been shown to induce bone formation in certain subjects. Non-limiting examples of statins that may be included in the devices of the present invention include atorvastatin, cerivastatin, fluvastatin, lovastatin, mavastatin, pitavastatin, pravastatin, rosuvastatin and simvastatin.

Immunosuppressants or anti-inflammatory agents that may be used in the devices of the present invention include cytokines, steroids, non-steroidal anti-inflammatories and agents that inhibit inflammatory cytokines. Compounds in one of these groups can also be characterized as being in another group. Examples of agents that inhibit inflammatory cytokines include, but are not limited to, tumor necrosis factor alph (TNF-α) inhibitors (Onercept, Adalimumab, Infliximab, Etanercept, Pegsunercept (PEG sTNF-R1), sTNF-R1, CDP-870, CDP-571, CNI-1493, RDP58, ISIS 104838, 1→3-β-D-glucans, Lenercept, PEG-sTNFRII Fc Mutein, D2E7, Afelimomab and antibodies or antibody fragments that bind to TNF-α or that bind to its receptor, inhibitors of TNF-α production or release (thalidomide, tenidap, and phosphodiesterase inhibitors, such as, but not limited to, pentoxifylline and rolipram), inhibitors of interleukin-1 (IL-1) such as Kineret® (anakinra) which is a recombinant, non-glycosylated form of the human interleukin-1 receptor antagonist (IL-1Ra), or AMG 108, which is a monoclonal antibody that blocks the action of IL-1, and any other antibody or antibody fragment that binds to IL-1 or its receptors), inhibitors of IL-6 (tocilizumab (a humanized anti-IL-6 mAb produced by Chugai Pharma USA, LLC, Bedminster, N.J.) or any other antibody or fragment that binds to IL-6 or its receptor), inhibitors of IL-8 (any antibody or antibody fragment that binds to IL-8 or its receptor), and inhibitors of nuclear factor kappa B (NFκB) (e.g., sulindac, clonidine, dexamethasone, flucinolonone, dithiocarbamate, and sulfasalazine).

Cytokines which have anti-inflammatory activity include, but are not limited to, interleukin-4 (IL-4) IL-10, IL-11, and IL-13.

Suitable examples of steroidal anti-inflammatory agents include, but are not limited to, hydrocortisone, cortisol, hydroxyltriamcinolone, alpha-methyl dexamethasone, dexamethasone-phosphate, clobetasol valerate, desonide, desoxymethasone, desoxycorticosterone acetate, dexamethasone, dichlorisone, diflorasone diacetate, diflucortolone valerate, fluadrenolone, flucrolone acetonide, fludrocortisone, flumethasone pivalate, fluocinolone acetonide, fluocinonide, flucortine butylesters, fluocortolone, fluprednidene (fluprednylidene) acetate, flurandrenolone, halcinonide, hydrocortisone acetate, hydrocortisone, methylprednisolone, triamcinolone acetonide, cortisol, cortisone, cortodoxone, flucetonide, fludrocortisone, difluorosone diacetate, fluradrenolone, fludrocortisone, diflurosone diacetate, fluocinolone, fluradrenolone acetonide, medrysone, amcinafel, amcinafide, betamethasone and the balance of its esters, chloroprednisone, chloroprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate and triamcinolone.

Further, suitable examples of non-steroidal anti-inflammatory compounds include, but are not limited to, acetaminophen, paracetamol, nabumetone, celecoxib, etodolac, nimesulide, apasone, gold, oxicams, such as piroxicam, isoxicam, meloxicam, tenoxicam, sudoxicam, and CP-14,304; the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

Antibiotics may also be included in various embodiments of the bone regeneration devices of the present invention (either during manufacture or prior to implantation) to help prevent or treat a bacterial infection. Suitable antibiotics include, but are not limited to, amikacin, gentamicin, kanamycin, neomycin, netilmicin, paromomycin, streptomycin, tobramycin and apramycin, streptovaricins, rifamycins, amoxicillin, ampicillin azlocillin, carbenicillin, cloxacillin, dicloxacillin, flucloxacillin, mezlocillin, nafcillin, piperacillin, pivampicillin, ticarcillin, cefacetrile, cefadroxil, cefalexin, cefaloglycin cefalotin, cefapirin cefazolin, cefradine, cefaclor, ceforanide, cefotiam cefprozil, cefuroxime, cefdinir, cefditoren, cefixime cefmenoxime, cefoperazone cefotaxime, cefpiramide, cefpodoxime, ceftazidime, ceftibuten, ceftriaxone, cefepime, cefquinome, sulbactam, tazobactam, clavulanic acid, ampicillin/sulbactam (sultamicillin), co-amoxiclav and combinations thereof.

Analgesic agents may also be included in various embodiments of the bone regeneration devices of the present invention. Suitable analgesic agents include, but are not limited to, acetaminophen, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof.

Suitable analgesics also include agents with analgesic properties, such as for example, amitriptyline, carbamazepine, gabapentin, pregabalin, clonidine, or a combination thereof.

Muscle relaxants may also be included in various embodiments of the bone regeneration devices of the present invention. Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The devices may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methyl and other paraben, polyvinyl alcohol and phenylethyl alcohol; solubility adjusting agents; stabilizers; and/or cohesion modifiers. Typically, any such inactive materials will be present within the range of 0-75 weight %, and more typically within the range of 0-30 weight %. In various embodiments, the devices may comprise sterile preservative free material.

Radiographic markers can be included on or in a bone regeneration device to permit the user to accurately position the device into the target site of the patient. These radiographic markers will also permit the user to track movement of the device at the site over time. In this embodiment, the user may accurately position a device in the site using any of the numerous diagnostic imaging procedures. Such diagnostic imaging procedures include, for example, X-ray imaging or fluoroscopy. Examples of such radiographic markers include, but are not limited to, barium, calcium and/or metal beads or particles. Where present, the radiographic marker is typically present in an amount of from about 10% to about 40% (including 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% and 40%, as well as ranges between any two of these values, e.g., 10-15%, 15-20%, 20-25%, 25-30%, 30-35%, 35-40%, and so forth, with 15-30% being more typical, even more typically 20-25%). In various embodiments, the radiographic marker could be a spherical shape or a ring around a device. In various embodiments, a radiographic marker is included in the bone regeneration device and the radiographic marker is a ceramic material.

In various embodiments, cells may be added to the bone regeneration device during manufacture or prior to implantation of a device in a subject. The cells can be pluripotent stem cells, totipotent stem cells, multipotent stem cells, mesenchymal stem cells, bone marrow stem cells, adipose-derived stem cells, endothelial stem cells and/or bone marrow cells. Stem cells may be derived from various tissue sources including, but not limited to, adipose tissue, muscle tissue, peripheral blood, cord blood, blood vessels, skeletal muscle, skin, liver and heart. The cells can also be stem cells that have begun differentiation into osteogenic precursor cells. The tissue may be harvested from autologous, allogenic or xenogenic sources; adult or embryonic tissue; a living donor or a cadaver. A xenogenic source is preferably an animal which is closely related to humans, such as a primate, or more preferably, a member of family Hominidae, such as gorilla or chimpanzee. The choice of a non-human source for the stem cells and bone marrow cells may be advantageous if it is avoids the legal, ethical, economic, and other concerns accompanying the use of human embryos or adults as the source of the stem cells and bone marrow cells. When cells are added during the preparation of a bone regeneration device prior to lyophilizing or freeze-drying, a compound such as Trehalose may need to be added to stabilize the cells.

The cells may also contain an expression vector containing a gene that encodes a therapeutic protein. The expression vector may be any plasmid or a viral vector, such as an adenovirus vector or retroviral vector, which constitutively expresses the desired gene. Alternatively, the expression vector can contain an inducible promoter which expresses the desired gene only when the desired conditions are present. The therapeutic protein could be a growth factor (such as those described above), a protein involved in bone regeneration or a protein that inhibits inflammation. Examples of such proteins are discussed above. Protocols for generating an expression vector containing a gene encoding a desired protein and for transfecting cells with the expression vector can be found in Sambrook & Russel, *Molecular Cloning, A Laboratory Manual*, Cold Spring Harbor Laboratory; 3rd edition (Jan. 15, 2001).

In various embodiments, a bone regeneration device may include enriched bone marrow fraction, prepared, for example, as described in U.S. Publication No. 2005/0130301, which is herein incorporated by reference thereto. As described therein, a bone marrow sample (e.g., from the subject to be treated) is centrifuged to separate the sample into fractions, including a fraction rich in connective tissue growth components. The fraction rich in connective tissue growth components can then be isolated from the other fractions, and incorporated into or onto the bone regeneration device, e.g., by using the fraction in or as a wetting medium applied to the bone regeneration device by a health care provider prior to implantation.

In various embodiments, a bone regeneration device may also include other biocompatible and preferably bioresorbable substances. These materials may include, for example, natural polymers such as proteins and polypeptides, glycosaminoglycans, proteoglycans, polynucleotides, polysaccharides, or combinations thereof. Non-limiting examples of natural polymers include elastin, purified collagen, hyaluronic acid, dermatan sulfate, silk, cellulose, starch, chitosans, gelatin, alginates, cyclodextrin, chondroitin sulfate and polydextrose. Synthetic polymers may also be incorporated into the devices of the present invention. Non-limited examples of synthetic polymers include biodegradable synthetic polymers such as polylactic acid, polyglycolide, polylactic polyglycolic acid copolymers ("PLGA"), polycaprolactone ("PCL"), vinylpyrrolidone, polyvinyl alcohol (PVA), PVA-g-PLGA, poly(dioxanone), poly(trimethylene carbonate) copolymers, polyglyconate, poly(propylene fumarate), poly(ethylene terephthalate), poly(butylene terephthalate), polyethylene glycol, polyethyleneglycol-terephtalate and poly-buthylene-terephtalate (PEGT-PBT) copolymer (polyactive), polyethylene glycol conjugates of poly(alpha-hydroxy acids), polyorthoesters, polyaspirins, polyphosphazenes, polycaprolactone copolymers, methacrylates, poly(N-isopropylacrylamide), polyethylene oxides (as known as polyoxyethylene or PEO), poly-propylene oxide (also known as polyoxypropylene or PPO), poly(aspartic acid) (PAA), PEO-PPO-PEO (Pluronics®, BASF), PEO-PPO-PAA copolymers, PLGA-PEO-PLGA, polyphosphoesters, polyanhydrides, polyester-anhydrides, polyhydroxybutyrate, polyhydroxyvalerate, tyrosine-derived polycarbonates, polyphosphazines, polytrimethylene carbonates, polyamide-esters, polyketals, polyacetals, polyethylene-vinyl acetates, silicones, polyurethanes, polypropylene fumarates, polydesaminotyrosine carbonates, polydesaminotyrosine arylates, polydesaminotyrosine ester carbonates, polydesamnotyrosine ester arylates, polyorthocarbonates, polycarbonates, and any random or (multi-)block copolymers, such as bipolymer, terpolymer, quaterpolymer, etc., that can be polymerized from the monomers related to previously-listed homo- and copolymers. The amount of other biocompatible and preferably bioresorbable substances within a bone regeneration device of the present invention, when present, can range from about 0.001% dry weight to about 25% dry weight, or about 0.01% dry weight to about 15% dry weight.

In some embodiments, the bone regeneration device can also include a mineral component. Any natural or synthetic mineral useful for bone in-growth or for structural support can be used. Non-limited examples of minerals include bioactive glass (such as, Bioglass®), tricalcium phosphate, biphasic calcium phosphate, hydroxyapatite, corraline hydroxyapatite and biocompatible ceramics. Biphasic calcium phosphate can have a tricalcium phosphate to hydroxyapatite weight ratio of about 50:50 to about 95:5, about 70:30 to about 95:5, about 80:20 to about 90:10 or about 85:15. The mineral component can be a granular particulate having an average particle diameter between about 0.2 and 5.0 mm, between about 0.4 and 3.0 mm or between about 0.4 and 2.0 mm. The amount of the mineral component within the bone regeneration device, when present, can range from about 0.001% dry weight to about 25% dry weight, or about 0.01% dry weight to about 15% dry weight.

In some embodiments, the mineral component can be bone particles, cancellous and/or cortical bone, ground to an average particle diameter between about 0.2 and 5.0 mm, between about 0.4 and 3.0 mm, and between about 0.4 and 2.0 mm. Both human and non-human sources of bone are suitable for use in the present invention and the bone may be autograft, allograft or xenograft in nature relative to the animal receiving the implant. Appropriate pre-treatments known in the art may be used to minimize the risks of disease transmission and/or immunogenic reaction when using bone particles as or in the mineral material.

Xenogenic bone can be pretreated to reduce or remove its immunogenicity. Such treated xenogenic bone provides a porous mineral component in the implant device. For example, the bone can be calcined or deproteinized to reduce the risks of immunogenic reactions to the implant material.

The pharmaceutical agents, when included in a bone regeneration device, can be provided in liquid formulations, for example buffered aqueous formulations, or as a powder that is reconstituted with water or in another aqueous formulation. In some embodiments, such liquid formulations can be poured upon, injected into, received upon and/or within, absorbed into or on, or otherwise combined with a dry-form of a bone regeneration device of the present invention by a health care provider just prior to implantation. In some embodiments, the pharmaceutical agents can be added to the bone regeneration device during the manufacturing of the device. In these embodiments, the bone regeneration device can be supplied to the end-user in a dry form or wet form. The inclusion of one or more pharmaceutical agents within or on the bone regeneration device during the manufacture of the bone regeneration device is uniquely possible because the temperature of the bone regeneration device does not exceed a temperature which could inactivate, denature or otherwise destroy pharmaceutical agents. Thus, one or more pharmaceutical agents can be incorporated into or on the device and stored in a dry format, then activated when the device is rehydrated prior to implantation or after implantation within a subject.

Pharmaceutical agents, such as those described above, can be incorporated homogeneously or regionally into a bone regeneration device by simple admixture or otherwise. Further, they can be incorporated alone or in conjunction with another carrier form or medium such as microspheres or another microparticulate formulation. Suitable techniques for forming microparticles are well known in the art and can be used to entrain or encapsulate pharmaceutically active agents whereafter the microparticles can be incorporated within or upon a bone regeneration device during or after its preparation.

A bone regeneration device can be implanted in a subject in a dry or wet condition. When the device is dried during manufacturing but rehydrated prior to implantation, any medically acceptable wetting agent can be used to rehydrate the device. Suitable wetting agents include, but are not limited to, aqueous substances such as sterile water, physiological saline, phosphate buffered saline, blood, bone marrow, bone marrow fractions or other liquid mediums, emulsions or suspensions that provide adequate wetting characteristics. Biocompatible organic liquids can also be used, alone or in combination with water. A wide variety of biocompatible organic liquids are known and suitable for these purposes, including for instance liquid polyols such as glycerol. In desired forms, molecules of the wetting agent (e.g., water) are taken up into the dried bone regeneration device to form a wet but firm bone regeneration device that retains its shape and cohesiveness.

In various embodiments, a method of treating a subject (human and non-human animals) having a bone defect by implanting in a subject a bone regeneration device as described herein is provided. The bone regeneration device can be implanted at a site at which bony tissue growth is desired, e.g. to treat a disease, defect or trauma, and/or in some instances to promote artificial arthrodesis. The bone regeneration device can be used as a surgical implant at, in, on, or near bone defect sites. In some embodiments, the bone regeneration device can exhibit a conformable or flexible character that enables its introduction and shaping within voids, defects or other areas in which new bone growth is desired, and/or in which the delivery of a pharmaceutical agent is desired. Furthermore, the bone regeneration device can have compression-resistant properties sufficient to resist substantial compression when impinged by adjacent soft tissues of the body at a bony implant site, for instance at a posterolateral spinal fusion implant site.

Illustrative bone repair sites that can be treated with a bone regeneration device of the present invention include those resulting from injury; defects brought about during the course of surgery, infection, or malignancy; and congenital or developmental defects. The bone regeneration devices of the present invention can be used in a wide variety of orthopedic, periodontal, neurosurgical and oral and maxillofacial surgical procedures including, but not limited to, the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; and cosmetic enhancement. Specific bones which can be repaired or replaced with the device include, but are not limited to, the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

Illustrative cartilage repair sites that may be treated with devices of the present invention include, as examples, articular cartilage surfaces occurring in articular joints having at least two major bones. Examples include, but are not limited to, the elbow, wrist, phalanx, knee, and ankle. Additionally, cartilage surfaces within shoulder and hip joints may be treated.

The bone regeneration devices of the present invention can be used as a bone void filler, bone healing composition, bone graft extender, bone graft enhancer or a bone graft replacement. The bone regeneration devices can be incorporated in, on or around a load bearing implants such as spinal implants, hip implants (e.g., in or around implant stems and/or behind acetabular cups), knee implants (e.g., in or around stems). Also, the bone regeneration devices can be incorporated in, on or around a load-bearing spinal implant device having a compressive strength of at least about 10000 N, such as a fusion cage, dowel, or other device potentially having a pocket, chamber or other cavity for containing an osteoinductive material, and used in a spinal fusion such as an interbody fusion. One illustrative use is in conjunction with a load-bearing interbody spinal spacer to achieve interbody fusion. In these procedures, the bone regeneration device can be placed in and/or around the spacer to facilitate the fusion.

The bone regeneration devices of the present invention can also be used with demineralized bone, partially demineralized bone, and/or non-demineralized bone in a layered configuration. In such embodiments, a layer of bone (demineralized, partially demineralized, and/or non-demineralized) has a layer of the bone regeneration device on either side of the bone layer. Alternatively, the bone regeneration device is covered with a layer of bone (demineralized, partially demineralized, and/or non-demineralized) on either side of the bone regeneration device. Some embodiments could have multiple layers of bone and the bone regeneration devices. Such layered embodiments may be useful to help hold bone pieces together or hold the bone pieces in the body of the subject where implanted. Such layered embodiments can provide a level of strength that may not be present when using a bone regeneration device by itself.

Kits are also provided which contain one or more bone regeneration devices. Such kits can include the bone regeneration device(s) described herein in a dried (e.g., having less than about 5% residual liquid) or wet format, received in sterile condition in medical packaging. The kit can also include, optionally, a pharmaceutical agent, such as BMP or other osteogenic proteins in solid or liquid form. A kit can also, optionally, include one or more additional surgical instruments or implants, for example a load-bearing implant (e.g., a spinal spacer), and/or a fluid transfer device such as a syringe, and/or a vial of sterile water, and/or instructions on usage of the various components of the kit. In one specific form, such a kit can include a dried device of the present invention, a BMP in lyophilized form (e.g. rhBMP-2) and an aqueous medium for reconstitution of the BMP to prepare an aqueous formulation that can then be added to the dried bone regeneration device. One suitable rhBMP-2 formulation is available from Medtronic, Memphis, Tenn., with its INFUSE® Bone Graft product. Such liquid formulations may be received upon and/or within, or otherwise combined with a dry-form device by a health care provider just prior to implantation.

In various embodiments, kits are provided which contain one or more bone regeneration devices in a wet form and osteogenic proteins or other biologically active agents provided in liquid formulations, for example buffered aqueous formulations. In other embodiments, such liquid formulations may be included within wet materials used to prepare a wetted device during its manufacture.

In various embodiments, methods of manufacturing or preparing a bone regeneration device are provided. One exemplary method comprises the following steps. First, soft tissue, such as collagen-rich tissue, fascia from an animal (including a human), etc., is obtained and gently cleansed to remove particles and substances that are not part of the soft tissue obtained. The soft tissue is then cut into pieces having a size as described above. The soft tissue is then mixed with a liquid such as water at a temperature not to exceed about 40° C. to make a soft tissue slurry. The amount of fascia to water can range from about 1:10 to about 1:200. The mixing equipment can be cooled to about −80° C., about −20° C., about 0° C., about 4° C., about 10° C., or even about 15° C. prior to the addition of the liquid and soft tissue so that temperature does not exceed about 40° C. during the mixing stage. The mixing is, optionally, stopped at various intervals so that the entire composition and the equipment can be cooled to a temperature sufficiently cold enough that the mixture does not exceed about 40° C. during the mixing stage. For example, the equipment and various components can be cooled to about −80° C., about −20° C., about 0° C., about 4° C., about 10° C., or even about 15° C. before and during the mixing stage. Alternatively, the mixing occurs in a "cold room" environment wherein the ambient air temperature is about 4° C. Bone derived material such as DBM, partially demineralized bone matrix or non-demineralized bone matrix, is added to the soft tissue slurry. The bone derived material has a size as described above to the soft tissue slurry, and the bone derived material and soft tissue slurry are mixed at a temperature not to exceed 40° C. (or with the essential absence of heating at a temperature above 40° C.) to make a soft tissue-bone derived material slurry. The total amount of soft tissue and bone derived material in the bone regeneration device can be as described above. The soft tissue-bone derived material slurry is then centrifuged at room temperature or less, and excess liquid is removed, leaving behind the soft tissue-bone derived material mixture. The soft tissue-bone derived material mixture is then poured into a mold and lyophilized or freeze-dried to produce a bone regeneration device. After freeze-drying or lyophilization, the bone regeneration device can be packaged and sterilized and the result is a dry form of the bone regeneration device. Alternatively, after removal of excess liquid, the bone regeneration device is poured into a mold, placed in packaging and sterilized resulting in a wet form of the bone regeneration device.

Another exemplary method of manufacturing or preparing a bone regeneration device comprises the following steps. First, bone derived material such as DBM or partially demineralized bone matrix having the size described above is mixed with a liquid such as water at a temperature not to exceed about 40° C. (or with the essential absence of heating at a temperature above 40° C.) to make a bone derived material slurry. The ratio of the amount bone derived material to liquid can be about the same ratio as the amount of soft tissue to liquid as described above (1:1 to 1:200). The mixing process can be stopped one or more times, as necessary, to cool the equipment and mixture so that the temperature does not exceed about 40° C. Soft tissue such as collagen-rich tissue, fascia, etc. that has been cleaned and cut to desired size, is then added to the bone derived material slurry. The components are then mixed in such a manner so that the temperature does not exceed about 40° C. (or with the essential absence of heating at a temperature above 40° C.), to produce a soft tissue-bone derived material slurry. The soft tissue-bone derived material slurry is then centrifuged at room temperature or less, and excess liquid is removed, leaving behind a soft tissue-bone derived material mixture. The soft tissue-bone derived material mixture is then poured into a mold and lyophilized or freeze-dried to produce a bone regeneration device. After freeze-drying or lyophilization, the bone regeneration device can be packaged and sterilized and the result is a dry form of the bone regeneration device. Alternatively, after removal of excess liquid, the bone regeneration device is poured into a mold, placed in packaging and sterilized resulting in a wet form of the bone regeneration device.

In the various methods of manufacturing or preparing a bone regeneration device of the present invention, soft tissue can be mixed with liquid, the bone derived material can be mixed with liquid, and/or the combination of the soft tissue, bone derived material and liquid can be mixed one, two, three or a multitude of times for 1 second, 5 seconds, 10 seconds, 15 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 or more hours (and includes every integer and fraction of the integers between these times). The mixing can occur at 4° C., room or ambient temperature or any temperature whereby the temperature of the components being mixed do not exceed about 40° C. The material being mixed and the mixer can be cooled in-between mixing cycles to about −80° C., about −20° C., about 0° C., about 4° C., about 10° C. or about 15° C. In one embodiment, the materials are blended together using a Waring® blender.

In the various methods of manufacturing or preparing a bone regeneration device of the present invention, one or more pharmaceutical agents can be added while mixing liquids with the soft tissue or the bone derived material or to the soft tissue and bone derived material slurry. As indicated above, because the temperature during processing does not exceed about 40° C., the one or more pharmaceutical agents are not destroyed, inactivated, or otherwise harmed during the processing. One of ordinary skill in the art can select an appropriate liquid that would not inactivate or otherwise harm the one or more pharmaceutical agents. It may not be necessary for the one or more pharmaceutical agents to be soluble in the liquid.

Alternatively, the various methods of manufacturing or preparing a bone regeneration device of the present invention may further comprise a step of wetting the bone regeneration device with one or more pharmaceutical agents prior to placing the bone regeneration device in a bone defect. The one or more pharmaceutical agents is selected from the group consisting of growth factors, statins, cells, antibiotics, and immunosuppressants.

In various embodiments, a method of treating a bone defect in a subject is provided. The method comprises placing in the bone defect a bone regeneration device comprising fascia and demineralized bone matrix. The bone regeneration device is prepared by (a) mixing a slurry of fascia with demineralized bone matrix with the essential absence of heating at a temperature above 40° C. to form a fascia-demineralized bone matrix slurry; (b) removing excess liquid from the fascia-demineralized bone matrix slurry; and (c) lyophilizing or freeze-drying the resulting slurry from step (b) into a bone regeneration device. The method may further comprise adding one or more pharmaceutical agents to the fascia-demineralized bone matrix slurry prior to step (b) wherein the one or more pharmaceutical agents is selected from the group consisting of growth factors, statins, cells, antibiotics, and immunosuppressants. Alternatively, the method may further comprise wetting the bone regeneration device with one or more pharmaceutical agents prior to placing the bone regeneration device in a bone defect wherein the one or more pharmaceutical agents is selected from the group consisting of growth factors, statins, cells, antibiotics, and immunosuppressants. In various embodiments, the one or more pharmaceutical agents comprises a growth factor selected from the group consisting of BMP-2, rhBMP-2, BMP-4, rhBMP4, BMP-6, rhBMP-6, BMP-7, rhBMP-7, GDF-5, rhGDF-5, functional fragments thereof and combinations thereof.

In still yet another exemplary embodiment, a slurry for preparing a bone regeneration device is provided. The slurry may comprise about 1 to 50% by weight fascia or about 1 to 20% by weight fascia, and about 1 to 50% by weight DBM or about 5 to 20% DBM, mixed at a temperature not exceeding 40° C. (or with the essential absence of heating at a temperature above 40° C.). The slurry may comprise one or more pharmaceutical agents selected from group consisting of growth factors, statins, cells, antibiotics, and immunosuppressants. In various embodiments, the slurry for preparing a bone regeneration device is provided and comprises about 3.5% by weight fascia and about 7 to 8% DBM mixed at a temperature not exceeding 40° C.

Treating or treatment of a bone defect or a condition refers to executing a protocol, which may include administering one or more devices to a patient (human, other normal or otherwise), in an effort to repair the bone defect or alleviate signs or symptoms of a condition. Alleviation can occur prior to signs or symptoms of the disease or condition appearing, as well as after their appearance. Thus, "treating" or "treatment" may include "preventing" or "prevention" of a disease or undesirable condition. In addition, "treating" or "treatment" does not require complete alleviation of signs or symptoms, does not require a cure, and specifically includes protocols that have only a marginal effect on the patient.

Having now generally described the invention, the same may be more readily understood through the following reference to the following examples, which are provided by way of illustration and are not intended to limit the present invention unless specified.

EXAMPLES

Example 1

Preparation of a Bone Regeneration Device

Fascia was obtained from CTS. It was cut into square pieces that are approximately 9.5 mm per side. 8.66 g of the fascia was weighed out and added to a Waring® blender containing 2.5 liters of water at 4° C. The fascia and water were blended for approximately 10 minutes to make a fascia slurry after which the blender was placed in −80° C. freezer for approximately 15 minutes to cool down the fascia slurry and the equipment. The fascia slurry was then blended again for approximately 10 minutes at 4° C.

Demineralized bone matix was obtained from CTS. The DBM was chopped up and then passed through a sieve having a pore size of between 100 to 710μ. 18.5 g of DBM were added to the fascia slurry and then blended for 30 seconds at room temperature (25° C.) to make a fascia-DBM slurry.

A portion of the blended fascia-DBM slurry was decanted into 50 ml centrifuge tubes and centrifuged at 2000 rpm for 10 minutes at room temperature. Excess water was decanted, leaving behind the fascia-DBM mixture. The fascia-DBM mixture was poured into a mold and lyophilized for at −80° C. for 24 hours. The resulting bone regeneration device is a flexible, porous sheet having a thickness of about 5 mm and exhibiting a bulk density in the range of about 0.17 g/cc to 0.21 g/cc. The sheet is then cut to desired strip sizes (approximately 2 cm×5 cm and approximately 2 cm×9 cm) and packaged in trays in a double-pouch format. The packaged products are terminally sterilized with an electron beam to a level of 25 kiloGrays (kGy). The bone regeneration device can be stored at room temperature until ready for use.

Example 2

Implantation of a Bone Regeneration Device

This Example is directed to an evaluation of the osteoinductivity of a formulation in which fascia is used as the carrier for DBM. In particular, a rat ectopic model will be used in this study. This model is a standard in the industry. DBM and Fascia were obtained from CTS and a bone regeneration device was prepared as provided in Example 1. The device was then cut into strips. In particular, the strips were cut into 8 mm cylinders. The strips were sterilized and then placed in a sterile Petri dish and hydrated with sterile water.

DBM particles were also obtained from CTS. The DBM particles were hydrated in sterile saline and packed into 1 cc syringes with the front end cut off. Excess water was pressed out until the 0.2 cc mark was reached.

Ten rats were used in this evaluation and they were athymic nude male rats which were at least 6 weeks old and weighed between 100 and 200 g. Each of the rats received either a strip placed intramuscularly in each of their hind limbs or a raw DBM implant placed intermuscularly in each of their hind limbs. The strips and DBM implants were placed close to the femur, but not touching the bone. All of the implants were sterilized during their preparation. The ten rats were grouped in 5 pairs and the composition of the implant received by each pair as well as the sterilization procedure used in preparing the implants is shown below in Table 1.

TABLE 1

| Group | Implant Composition | Sterilization |
|---|---|---|
| Group 1 | Fascia/DBM Strip | Gamma 15 kGY, Dry Ice |
| Group 2 | DBM | Gamma 15 kGY, Dry Ice |
| Group 3 | Fascia/DBM Strip | E-beam 15 kGy, Frozen |
| Group 4 | DBM | E-beam 15 kGy, Frozen |
| Group 5 | Aseptic DBM | None |

Group 1 and 3 rats received a strip implant containing fascia and DBM. The implants used for Group 1 rats were sterilized with gamma irradiation while the implants used for Group 3 rats were sterilized with e-beam irradiation. Group 2 and 4 rats both received DBM implants. The implants used for Group 2 rats were sterilized by gamma irradiation while the implants used for Group 4 rats were sterilized using e-beam irradiation. Group 5 rats received aseptic DBM implants and were included as a control to evaluate the osteoinductivity of raw DBM in the absence of irradiation. All of the rats were sacrificed at 4 weeks and their histology was evaluated.

Specimens were obtained from each of the rats. First, the femur of each rat was trimmed and excess soft tissue was dissected and discarded. Each specimen was then stored in 10% neutral buffered formalin. The specimens were then decalcified using standard procedures and paraffin embedding of the decalcified specimens were then performed using standard procedures. Each specimen was centered in a block before the embedding in paraffin and the blocks were sectioned using standard procedures. The sections were then stained using standard procedures.

Bone formation was then evaluated with respect to bone response, bone quality, inflammation, tissue reaction and the implant material. The rats as mentioned above were sacrificed at 4 weeks and therefore bone formation was evaluated at 4 weeks after implantation. A score between 0 and 4 was then provided which is based on the amount of bone formation. A score of 0 reflects no bone formation, a score of 1 reflects about 1 to 25% bone formation, a score of 2 reflects about 26 to 50% bone formation, a score of 3 reflects about 51 to 75% bone formation and a score of 4 reflects about 76 to 100% bone formation. The results of the 5 test groups are shown below in Table 2.

TABLE 2

| Group | Implant Composition | Sterilization | Score |
|---|---|---|---|
| 1 | Fasica/DBM | 15 kGy Gamma | 1 |
| 2 | DBM | 15 kGy Gamma | 3 |
| 3 | Fasica/DBM | 15 kGy E-beam | 2 |
| 4 | DBM | 15 kGy E-beam | 1 |
| 5 | Aseptic DBM | N/A | 4 |

As is readily apparent from Table 2, rats receiving strip implants comprising fascia and DBM which were sterilized by e-beam irradiation had surprising bone formation (about 26 to 50% bone formation). Commonly, as known by one skilled in the art, sterilization of implants reduces bone formation to less than 25%.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A bone regeneration device comprising fascia and demineralized bone matrix mixed at a temperature not exceeding about 40° C. and lyophilized into said bone regeneration device, wherein the fascia is between about 1% to 45% of the dry weight of said bone regeneration device and the demineralized bone matrix is between about 55% to 99% of the dry weight of said bone regeneration device, wherein the bulk density of the bone regeneration device is between about 0.1 g/cc to 0.4 g/cc.

2. A bone regeneration device according to claim 1, wherein the fascia and demineralized bone matrix are mixed at a temperature not exceeding about 25° C.

3. A bone regeneration device according to claim 1, wherein the dry weight ratio of fascia to demineralized bone matrix is between about 1:15 to 1:1.

4. A bone regeneration device according to claim 1, further comprising one or more pharmaceutical agents selected from the group consisting of growth factors, statins, cells, antibiotics, and immunosuppressants.

5. A bone regeneration device according to claim 1, wherein the bone regeneration device comprises a statin.

6. A bone regeneration device according to claim 1, wherein the device comprises a void volume range of about 40% to about 90%.

* * * * *